US00PP31468P2

(12) United States Plant Patent
Miyazaki

(10) Patent No.: US PP31,468 P2
(45) Date of Patent: Feb. 18, 2020

(54) ***TORENIA* PLANT NAMED 'SUNRENI SANIMIYA'**

(50) Latin Name: ***Torenia* sp.**
Varietal Denomination: Sunreni Sanimiya

(71) Applicant: Kiyoshi Miyazaki, Shiga (JP)

(72) Inventor: Kiyoshi Miyazaki, Shiga (JP)

(73) Assignee: Suntory Flowers Limited, Tokyo (JP)

( * ) Notice: Subject to any disclaimer, the term of this patent is extended or adjusted under 35 U.S.C. 154(b) by 0 days.

(21) Appl. No.: 16/350,931

(22) Filed: Feb. 1, 2019

(51) Int. Cl.
*A01H 5/02* (2018.01)
*A01H 6/00* (2018.01)

(52) U.S. Cl.
USPC ..... Plt./487
CPC ..... *A01H 6/00* (2018.05)

(58) Field of Classification Search
USPC ..... Plt./487
CPC ..... A01H 5/02
See application file for complete search history.

*Primary Examiner* — Kent L Bell
(74) *Attorney, Agent, or Firm* — C. A. Whealy

(57) ABSTRACT

A new and distinct cultivar of *Torenia* plant named 'Sunreni Sanimiya', characterized by its compact, semi-upright, mounding to trailing plant habit; vigorous growth habit; freely branching habit; relatively short internodes; freely flowering habit; large dark violet, violet and violet blue-colored flowers; and good garden performance.

1 Drawing Sheet

Botanical designation: *Torenia* sp.
Cultivar denomination: 'SUNRENI SANIMIYA'.

BACKGROUND OF THE INVENTION

The present invention relates to a new and distinct cultivar of *Torenia* plant, botanically known as *Torenia* sp. and hereinafter referred to by the name 'Sunreni Sanimiya'.

The new *Torenia* plant is a product of a planned breeding program conducted by the Inventor in Higashiomi, Shiga, Japan. The objective of the breeding program is to develop new trailing and freely branching *Torenia* plants with numerous large attractive flowers.

The new *Torenia* plant originated from a cross-pollination in Higashiomi, Shiga, Japan in June, 2012 of a proprietary selection of *Torenia* sp. identified as code designation BR4X, not patented, as the female, or seed parent with a proprietary selection of *Torenia* sp. identified as code designation TNC-W, not patented, as the male, or pollen, parent. The new *Torenia* plant was discovered and selected by the Inventor as a single flowering plant from within the progeny of the stated cross-pollination in a controlled greenhouse environment in Higashiomi, Shiga, Japan in May, 2013.

Asexual reproduction of the new *Torenia* plant by vegetative cuttings in a controlled greenhouse environment in Higashiomi, Shiga, Japan since April, 2014 has shown that the unique features of this new *Torenia* plant are stable and reproduced true to type in successive generations.

SUMMARY OF THE INVENTION

Plants of the new *Torenia* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Sunreni Sanimiya'. These characteristics in combination distinguish 'Sunreni Sanimiya' as a new and distinct *Torenia* plant:

1. Compact, semi-upright, mounding to trailing plant habit.
2. Vigorous growth habit.
3. Freely branching habit.
4. Relatively short internodes.
5. Freely flowering habit.
6. Large dark violet, violet and violet blue-colored flowers.
7. Good garden performance.

Plants of the new *Torenia* differ primarily from plants of the female parent selection in branching habit as plants of the new *Torenia* plant are more freely branching than plants of the female parent selection.

Plants of the new *Torenia* differ primarily from plants of the male parent selection in flower color as plants of the new *Torenia* plant have dark violet, violet and violet blue-colored flowers whereas plants of the male parent selection have white-colored flowers.

Plants of the new *Torenia* can be compared to plants of *Torenia* 'Sunrenilabu', disclosed in U.S. Plant Pat. No. 10,843. In side-by-side comparisons, plants of the new *Torenia* and 'Sunrenilabu' differ primarily in the following characteristics:

1. Plants of the new *Torenia* are semi-upright whereas plants of 'Sunrenilabu' are horizontally spreading.
2. Plants of the new *Torenia* are more compact than plants of 'Sunrenilabu'.
3. Plants of the new *Torenia* are more freely branching than plants of 'Sunrenilabu'.
4. Plants of the new *Torenia* have shorter internodes than plants of 'Sunrenilabu'.
5. Plants of the new *Torenia* and 'Sunrenilabu' differ in flower color as plants of the new *Torenia* have dark violet, violet and violet blue-colored flowers whereas plants of 'Sunrenilabu' have light violet and violet-colored flowers.

6. Plants of the new *Torenia* have shorter peduncles than plants of 'Sunrenilabu'.

BRIEF DESCRIPTION OF THE PHOTOGRAPHS

The accompanying colored photographs illustrate the overall appearance of the new *Torenia* plant showing the colors as true as it is reasonably possible to obtain in colored reproductions of this type. Colors in the photographs may differ slightly from the color values cited in the detailed botanical description which accurately describe the colors of the new *Torenia* plant.

The photograph at the top of the sheet comprises a side perspective view of a typical flowering plant of 'Sunreni Sanimiya' grown in a container.

The photograph at the bottom of the sheet is a close-up view of typical flowers of 'Sunreni Sanimiya'.

DETAILED BOTANICAL DESCRIPTION

The aforementioned photographs and following observations, measurements and values describe plants grown during the summer in 24-cm containers in an outdoor nursery in Higashiomi, Shiga, Japan and under cultural practices typical for commercial *Torenia* production. During the production of the *Torenia* plants, day temperatures averaged 23° C. and night temperatures averaged 15° C. Plants were eight months old when the photographs and description were taken. In the following description, color references are made to The Royal Horticultural Society Colour Chart, 2015 Edition, except where general terms of ordinary dictionary significance are used.

Botanical classification: *Torenia* sp. 'Sunreni Sanimiya'.

Parentage:

*Female, or seed, parent.*—Proprietary selection of *Torenia* sp. identified as code designation BR4X, not patented.

*Male, or pollen, parent.*—Proprietary selection of *Torenia* sp. identified as code designation TNC-W, not patented.

Propagation:

*Type.*—By vegetative cuttings.

*Time to initiate roots.*—About one week at temperatures about 20° C. to 25° C.

*Time to produce a rooted young plant.*—About three to four weeks at temperatures about 15° C. to 20° C.

*Root description.*—Fibrous; typically white in color, actual color of the roots is dependent on substrate composition, water quality, fertilizer type and formulation, substrate temperature and physiological age of roots.

*Rooting habit.*—Freely branching.

Plant description:

*Plant and growth habit.*—Compact, semi-upright, mounded to trailing plant habit; vigorous growth habit; freely branching habit with numerous lateral branches developing per plant, pinching enhances branching potential.

*Plant height.*—About 25 cm.

*Plant width (spread).*—About 77 cm.

*Lateral branches.*—Length: About 31 cm. Diameter: About 1.9 mm. Internode length: About 4.7 cm. Aspect: Upright to outwardly orientate. Texture: Sparsely pubescent. Color: Close to 144B; at the internodes, tinged with close to 177B.

Leaf description:

*Arrangement.*—Opposite, simple.

*Length.*—About 3.3 cm.

*Width.*—About 2.5 cm.

*Shape.*—Ovate.

*Apex.*—Acute.

*Base.*—Cordate.

*Margin.*—Dentate.

*Texture, upper and lower surfaces.*—Sparsely pubescent.

*Venation pattern.*—Pinnate; reticulate.

*Color.*—Developing leaves, upper surface: Close to 137C. Developing leaves, lower surface: Close to 146B. Fully expanded leaves, upper surface: Close to N137D; venation, close to 145A. Fully expanded leaves, lower surface: Close to 147B; venation, close to 145B.

*Petioles.*—Length: About 7.5 mm. Diameter: About 1.5 mm. Texture, upper and lower surfaces: Sparsely pubescent. Color, upper surface: Close to 146B. Color, lower surface: Close to 144B.

Flower description:

*Flower form and flowering habit.*—Single flowers borne in upper leaf axils or terminally; corolla bilabiate and calyx tubular; flowers face upright to outwardly; freely flowering habit with about 142 flowers developing per plant.

*Fragrance.*—None detected.

*Natural flowering season.*—Plants begin flowering about three to four weeks after planting rooted cuttings; long flowering period; continuously flowering from early summer to late autumn in Japan.

*Postproduction longevity.*—Flowers last about four days on the plant; flowers persistent.

*Flower buds.*—Height: About 1.7 cm. Diameter: About 8.3 mm. Shape: Ellipsoidal. Color: Close to N88A.

*Flower diameter.*—About 3 cm.

*Flower depth.*—About 3.6 cm.

*Throat diameter.*—About 1 cm.

*Tube diameter, base.*—About 3.5 mm.

*Tube length.*—About 2 cm.

*Petals.*—Quantity per flower: Bilabiate with one upper or banner petal with two fused lobes and one lower petal with two lateral lobes and a single lower lobe, petals fused. Upper petal, fused lobes: Length: About 1.5 cm. Width: About 2.5 cm. Shape: Elliptic. Apex: Cuspidate to mucronate. Margin: Entire; undulate. Texture, upper and lower surfaces: Smooth, glabrous; velvety. Color: Developing, upper surface: Close to 85B. Developing, lower surface: Close to N88B; towards the margins, close to N88D. Fully developed, upper surface: Close to 91B. Fully developed, lower surface: Close to N88C; towards the margins, close to 91C. Lower petal, lateral lobes: Length: About 1.1 cm. Width: About 1.7 cm. Shape: Elliptic. Apex: Rounded. Margin: Entire; slightly undulate. Texture, upper and lower surfaces: Smooth, glabrous; velvety. Color: Developing, upper surface: Close to 83A; towards the margins, close to N88D. Developing, lower surface: Close to 83A. Fully developed, upper surface: Close to 83A; towards the margins, close to N88D. Fully developed, lower surface: Close to 85B. Lower petal, lower lobe: Length: About 1.4 cm. Width: About 1.7 cm. Shape: Roughly circular. Apex: Rounded. Margin: Entire; slightly undulate. Texture, upper and lower surfaces: Smooth, glabrous; velvety. Color: Developing, upper surface: Close to 83A; towards the margins, close to N88D; towards the base, close to 85B. Developing, lower surface: Close to 86B; towards the base, close to 85D. Fully developed, upper surface: Close to N87A; towards the base, close to 85C. Fully developed, lower surface: Close to 86D; towards the base, close to 85D. Throat texture: Smooth, glabrous. Throat color: Distally, close to 86B; mid-section, close to 85B; proximally, close to 85D. Tube texture: Pubescent. Tube color: Distally, close to 85A; mid-section, close to 86A; proximally, close to 163B.

*Sepals.*—Quantity per flower: Typically five, fused. Length: About 6.3 mm. Width: About 5.3 mm. Shape: Lanceolate. Apex: Acuminate. Margin: Entire. Texture, upper surface: Smooth, glabrous. Texture, lower surface: Pubescent. Color, immature, upper and lower surfaces: Close to 144B. Color, mature, upper and lower surfaces: Close to 144B.

*Peduncles.*—Length: About 1.1 cm. Diameter: About 1.3 mm. Aspect: Upright to outwardly. Texture: Pubescent. Color: Close to 144B.

*Reproductive organs.*—Stamens: Quantity per flower: Typically four; two pairs of fused anthers. Filament length: About 4.2 mm to 10.7 mm. Anther shape: Ellipsoidal. Anther size: About 1.5 mm by 4.4 mm. Anther color: Close to NN155C tinged slightly with close to 84D. Pollen amount: Moderate. Pollen color: Close to NN155A. Pistils: Quantity per flower: One. Pistil length: About 1.9 cm. Stigma shape: Bi-parted. Stigma color: Close to N155D. Style color: Close to N155B. Ovary color: Close to 144A.

*Seeds and fruits.*—To date, seed and fruit development have not been observed on plants of the new *Torenia.*

Pathogen & pest resistance: To date, plants of the new *Torenia* have not been noted to be resistant to pathogens and pests common to *Torenia* plants.

Garden performance: Plants of the new *Torenia* have been observed to have good garden performance and to tolerate rain, wind and temperatures ranging from about 5° C. to about 30° C.

It is claimed:

1. A new and distinct *Torenia* plant named 'Sunreni Sanimiya' as illustrated and described.

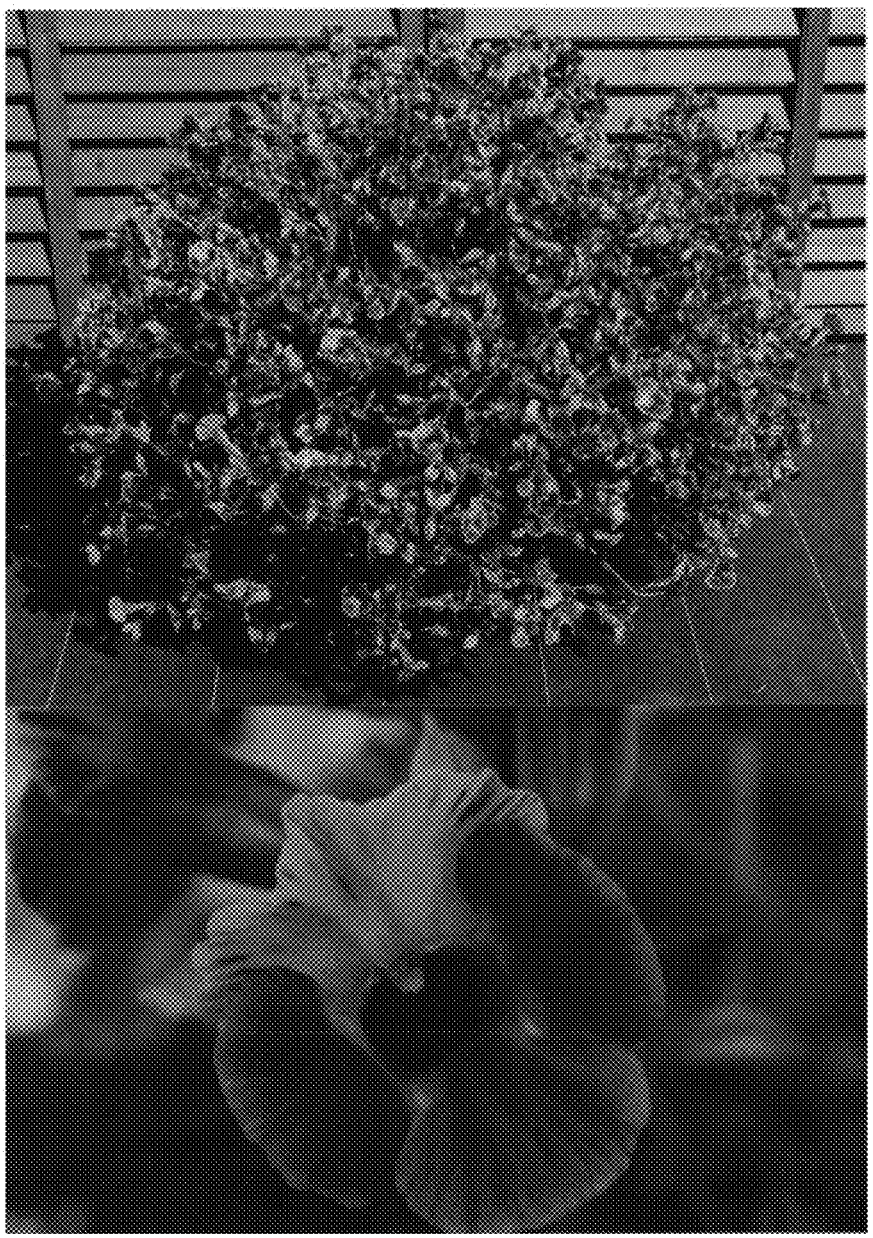

* * * * *